(12) United States Patent
Kusumoto et al.

(10) Patent No.: US 9,103,781 B2
(45) Date of Patent: Aug. 11, 2015

(54) SAMPLE SEPARATION AND ADSORPTION APPLIANCE

(75) Inventors: Kouji Kusumoto, Osaka (JP); Yutaka Unuma, Osaka (JP); Hideki Kinoshita, Osaka (JP); Shinichi Goto, Osaka (JP); Tsuyoshi Tanaka, Osaka (JP); Yuji Maruo, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/343,528

(22) PCT Filed: Sep. 12, 2011

(86) PCT No.: PCT/JP2011/070754
§ 371 (c)(1),
(2), (4) Date: Mar. 7, 2014

(87) PCT Pub. No.: WO2013/038474
PCT Pub. Date: Mar. 21, 2013

(65) Prior Publication Data
US 2014/0224657 A1    Aug. 14, 2014

(51) Int. Cl.
*G01N 27/447* (2006.01)
(52) U.S. Cl.
CPC .... *G01N 27/44773* (2013.01); *G01N 27/44739* (2013.01)
(58) Field of Classification Search
CPC .......... G01N 27/447; G01N 27/44704; G01N 27/44739; G01N 27/44756; G01N 27/44773–27/44778
USPC ................... 204/456–470, 606–621
See application file for complete search history.

(56) References Cited

U.S. PATENT DOCUMENTS

| 4,631,120 A | 12/1986 | Pohl |
| 5,126,025 A | 6/1992 | Carson et al. |
| 2011/0094887 A1 | 4/2011 | Midorikawa et al. |

FOREIGN PATENT DOCUMENTS

| JP | 4-264253 A | 9/1992 |
| JP | 2010-8376 A | 1/2010 |
| JP | 2011-145137 A | 7/2011 |
| JP | 2011-196914 A | 10/2011 |

OTHER PUBLICATIONS

Machine translation of JP 2011-145137, A.*
Official Communication issued in International Patent Application No. PCT/JP2011/070754, mailed on Oct. 25, 2011.

* cited by examiner

*Primary Examiner* — J. Christopher Ball
(74) *Attorney, Agent, or Firm* — Keating & Bennett, LLP

(57) ABSTRACT

A sample separation and adsorption appliance (100) includes a negative electrode (2), a positive electrode (3), a sample separation unit (6) that has a first opening (17) opened to a side facing the negative electrode (2) and a second opening (18) opened to a side facing the positive electrode (3), the sample separation unit containing a separation gel (7), and a slit structure (8) including a slit (1) at a position facing the second opening (18). A transfer film (9) is arranged between the second opening (18) and the slit (1).

10 Claims, 14 Drawing Sheets

(a)

(b)

(c)

SAMPLE SEPARATION AND ADSORPTION APPLIANCE

TECHNICAL FIELD

The present invention relates to a sample separation and adsorption appliance for separating a sample in a separation medium, and subsequently adsorbing the separated sample onto a sample adsorption member.

BACKGROUND ART

In the field of proteome analysis taking a primary role in post-genome researches, a combination of two-dimensional electrophoresis (2DE) and Western blotting is known as an excellent separation analysis method. The 2DE is capable of separating proteome into a plurality of components (proteins) with high resolution by employing various separation media on the basis of two independent physical properties (electric charge and molecular weight) that are specific to each protein. When further analyzing proteins by utilizing the separation result obtained with the 2DE, it is preferable to fixate plural proteins, which are contained in the separation medium, to a transfer film by the Western blotting. This is because the protein fixated to the transfer film can be preserved in a stable state for a long term and is easier to analyze. The Western blotting can be said as being an essential process particularly when biological features, such as an increase or decrease of expression and the presence or absence of posttranslational modification, of plural proteins are to be comparatively studied in an exhaustive manner by utilizing the separation result obtained with the 2DE.

Independent devices for the 2DE and the Western blotting have been employed up to date. This implies the necessity of operations of taking out the separation medium from an electrophoresis device after the electrophoresis, moving the separation medium into a transfer device, and setting a transfer film in the transfer device to perform a transfer process. When the manual operations by a researcher are interposed between the electrophoresis and the transfer as described above, a problem arises in that reproducibility of the obtained result reduces. Furthermore, because the separation medium to be handled is a very soft and breakable gel, expert skills are needed to carry out the Western blotting.

Meanwhile, regarding capillary electrophoresis (CE) using a capillary, Patent Literature (PTL) 1 proposes a technique for carrying out the electrophoresis and the transfer in one device. More specifically, the proposed technique can make a sample, which is discharged through a capillary (filled with a gel or a solution), adsorbed directly onto a transfer film and can recover the sample in one device. According to the proposed technique, the electrophoresis and the transfer can be performed continuously.

CITATION LIST

Patent Literature

PTL 1: Japanese Unexamined Patent Application Publication No. 4-264253 (Laid-open on Sep. 21, 1992)

SUMMARY OF INVENTION

Technical Problem

With the technique disclosed in PTL 1, however, when the sample separated by the electrophoresis is adsorbed onto the transfer film, a minimum value of resolution is determined by the diameter of a distal end of the capillary in theory, and higher resolution than a theoretical limit cannot be obtained. Moreover, in a practical transfer process, the sample discharged from the capillary diffuses during a period in which the sample is adsorbed onto the transfer film, and an adsorption pattern of the sample on the transfer film becomes blurred in some cases. In addition, because the technique disclosed in PTL 1 is a technique of transferring the sample as it is after being migrated with the capillary electrophoresis, it is impossible in principle to realize separation and development in two-dimensional directions.

To solve the above-mentioned problems, an object of the present invention is to realize sample adsorption with high resolution in a sample separation and adsorption appliance, which can continuously perform transfer after second dimensional electrophoresis.

Solution to Problem

In trying to continuously perform the electrophoresis and the transfer, the inventors have found a blotting method of transferring separated molecules to a transfer film from an end surface of an electrophoresis medium by utilizing a pair of electrodes used for the electrophoresis, and have realized sample adsorption with high resolution according to that blotting method.

To achieve the above object, more specifically, the present invention provides a sample separation and adsorption appliance for separating a sample in a separation medium by applying a current to the separation medium through a buffer solution, and for adsorbing the separated sample onto a sample adsorption member from the separation medium, the sample separation and adsorption appliance comprising a first electrode, a second electrode, a sample separation unit that has a first opening opened to a side facing the first electrode and a second opening opened to a side facing the second electrode, the sample separation unit containing the separation medium, and a slit structure including a slit at a position facing the second opening, wherein the sample adsorption member is arranged between the second opening and the slit.

According to the features described above, since the sample separation unit containing the separation medium has the first opening and the second opening, the first electrode and the second electrode are electrically connected to each other through the buffer solution, the separation medium, and the sample adsorption member upon application of a voltage between the first electrode and the second electrode. Furthermore, the slit arranged at the position facing the second opening acts to converge the lines of electric force, which advance from the first electrode toward the second electrode.

Upon the application of the voltage between the first electrode and the second electrode, the sample is caused to migrate through the separation medium and is separated into plural components. The separated sample components flow along the lines of electric force even after being discharged from the second opening, and they are adsorbed onto the sample adsorption member.

Here, since the sample adsorption member is arranged between the second opening and the slit, the lines of electric force pass through the sample adsorption member while being converged toward the slit from the second opening. In other words, the sample flowing along the lines of electric force is converged in a process during which the sample is discharged from the second opening and is adsorbed onto the sample adsorption member.

According to the features described above, therefore, it is possible to suppress spreading of sample adsorption with respect to the sample adsorption member, and to realize the sample adsorption with higher resolution.

In the case of adsorbing the separated sample onto the sample adsorption member from the separation medium, a sample separation pattern can be obtained by moving the sample adsorption member in a second direction perpendicular to a first direction that is specified by the first electrode and the second electrode.

Moreover, according to the features described above, the second dimensional electrophoresis and the transfer can be continuously performed by setting, as the sample, a separation medium that has been subjected to the first dimensional electrophoresis.

Advantageous Effects of Invention

In a sample separation and adsorption appliance for separating a sample in a separation medium by applying a current to the separation medium through a buffer solution, and for adsorbing the separated sample onto a sample adsorption member from the separation medium, according to the present invention, the sample separation and adsorption appliance includes a first electrode, a second electrode, a sample separation unit that has a first opening opened to a side facing the first electrode and a second opening opened to a side facing the second electrode, the sample separation unit containing the separation medium, and a slit structure including a slit at a position facing the second opening, wherein the sample adsorption member is arranged between the second opening and the slit. Therefore, the sample adsorption with higher resolution can be realized in the sample separation and adsorption appliance that is capable of continuously carrying out a process from the second dimensional electrophoresis to the transfer.

DESCRIPTION OF EMBODIMENTS

One embodiment of the present invention will be described below with reference to the drawings.

(Sample Separation and Adsorption Appliance 100)

Figure 1:
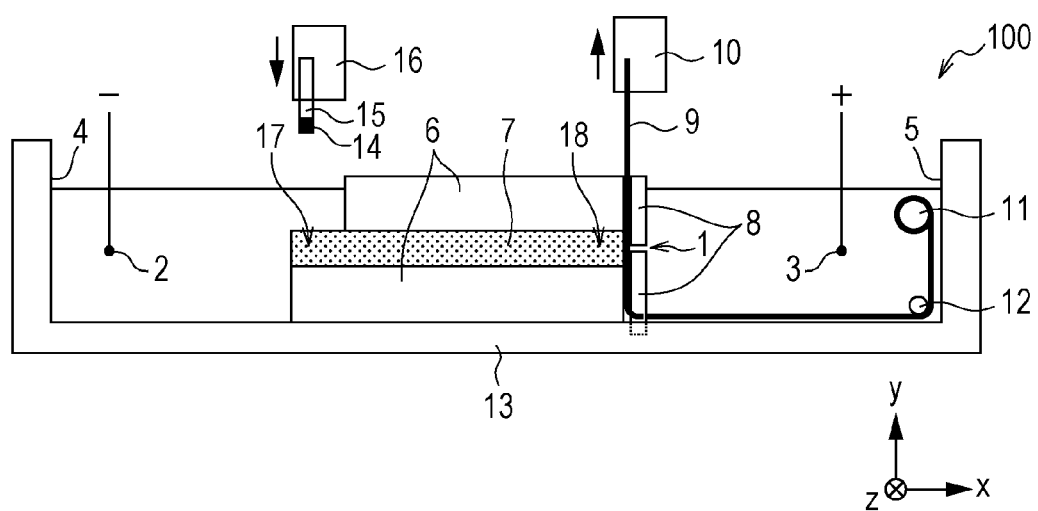
FIG. 1 is a sectional view illustrating a basic structure of a sample separation and adsorption appliance according to one embodiment of the present invention.

First, a basic structure of a sample separation and adsorption appliance 100 according to the embodiment will be described below with reference to FIG. 1. FIG. 1 is a sectional view illustrating the basic structure of the sample separation and adsorption appliance 100. It is to be noted that the sample separation and adsorption appliance 100 is a horizontally-installed device in which a sample is separated substantially in the horizontal direction. However, the sample separation and adsorption appliance of the present invention is not limited to the horizontally-installed device, and it may be a vertically-installed device.

As illustrated in FIG. 1, the sample separation and adsorption appliance 100 includes a negative electrode (first electrode) 2, a positive electrode (second electrode) 3, a first buffer solution tank 4, a second buffer solution tank 5, a sample separation unit 6 containing a separation gel (separation medium) 7, a slit structure 8 forming a slit 1, and two moving arms 10 and 16. A transfer film (sample adsorption member) 9 is arranged between the sample separation unit 6 and the slit 1.

The sample separation unit 6 has a first opening 17 opened toward the first buffer solution tank 4 and a second opening 18 opened toward the second buffer solution tank 5. In the sample separation and adsorption appliance 100, therefore, when the first buffer solution tank 4 and the second buffer solution tank 5 are filled with buffer solutions, the negative electrode 2 in the first buffer solution tank 4 and the positive electrode 3 in the second buffer solution tank 5 are electrically connected to each other through the buffer solutions in both the tanks, the separation gel 7, and the transfer film 9. Thus, upon application of a voltage between the negative electrode 2 and the positive electrode 3, the sample separation and adsorption appliance 100 operates to separate a sample, which is introduced from the first opening 17, in the separation gel 7, and to discharge separated individual components of the sample through the second opening 18 to be adsorbed onto the transfer film 9.

Main members of the sample separation and adsorption appliance will be described in detail below with reference to FIG. 1.

It is to be noted that, in the following description, a sample separation direction defined with respect to the negative electrode 2 and the positive electrode 3 in the sample separation and adsorption appliance 100 is an x-axis direction, a moving direction of the transfer film 9 is a y-axis direction, and a direction perpendicular to both the x-axis and the y-axis is a z-axis direction.

(Negative Electrode 2 and Positive Electrode 3)

The negative electrode 2 is arranged in the first buffer solution tank 4, and the positive electrode 3 is arranged in the second buffer solution tank 5. The negative electrode 2 and the positive electrode 3 are each made of a material having electrical conductivity, such as a metal. The material used to form the negative electrode 2 and the positive electrode 3 is preferably platinum, for example, from the viewpoint of suppressing ionization of the electrodes.

Regarding electrode layout, the negative electrode 2, the second opening 18, and the positive electrode 3 are preferably arranged substantially on one linear line. In such electrode layout, when the transfer film 9 is arranged as illustrated in FIG. 1, the lines of electric force passing through the second opening 18 are substantially perpendicular to the transfer film 9. Hence accuracy of the sample adsorption can be improved.

Furthermore, the positive electrode 3 is preferably arranged far away from the transfer film 9. Such an arrangement can suppress bubbles, which are generated from the positive electrode 3, from adversely affecting adsorption of the separated components onto the transfer film 9.

(First Buffer Solution Tank 4 and Second Buffer Solution Tank 5)

The first buffer solution tank 4 and the second buffer solution tank 5 are formed by mounting the sample separation unit 6 in a stage 13 in the form of a container such that the stage 13 is divided into two tanks.

The buffer solutions contained in the first buffer solution tank 4 and the second buffer solution tank 5 may be any type of buffer solution having electrical conductivity. However, there is a possibility that a buffer solution having a buffer zone in a highly acidic or highly basic range may adversely affect both the separation gel 7 and the transfer film 9.

(Sample Separation Unit 6)

The sample separation unit 6 has, as described above, the first opening (sample supply medium connection portion) 17 opened toward the first buffer solution tank 4 and the second opening (sample component discharge port) 18 opened toward the second buffer solution tank 5. The sample separation unit 6 contains the separation gel 7 therein, and the separation gel 7 faces the inside of the first buffer solution tank 4 through the first opening 17 and the inside of the second buffer solution tank 5 through the second opening 18.

The sample separation unit 6 can be constituted by two plates that are each made of an insulator, e.g., glass or acryl. Of the two plates, the plate arranged on the upper side is preferably partly cut out on the side close to the first opening 17. With the presence of the cutout, an upper surface of the separation gel 7 on the side close to the first opening 17 is exposed, and the sample can be introduced through an exposed portion in the upper surface of the separation gel 7.

The separation gel 7 acts to separate individual components of the sample, which is introduced through the first opening 17, depending on molecular weights. The separation gel 7 is filled in the sample separation unit 6 before or after the sample separation unit 6 is mounted to the stage 13. The separation gel 7 is, for example, an acrylamide gel or an agarose gel.

While, in this embodiment, the separation gel 7 is filled in the sample separation unit 6, many hyperfine columns, called nano-pillars, may be disposed between the two opposing plates that constitute the sample separation unit 6.

The second opening 18 of the sample separation unit 6, including the surroundings thereof, may be covered with a cover member (electrically conductive medium: not illustrated), which is made of a porous material. The presence of the cover member is effective in, when the transfer film 9 is contacted with or pressed against the second opening 18 (i.e., when there is no distance between the second opening 18 and the transfer film 9), reducing friction resistance and damage that the transfer film 9 may receive from the sample separation unit 6 and the separation gel 7 with conveying of the transfer film 9.

The porous material of the cover member is preferably a material that has fine pores penetrating thoroughly, hydrophillicity, low sample adsorption capacity, and high strength. The cover member made of such a material and positioned in a path through which the separated components pass allows the separated components to pass satisfactorily therethrough.

For example, in the case of the porous material having fine pores penetrating thoroughly and hydrophillicity, when the separation gel 7 is filled, the separation gel 7 is sufficiently filled into not only the second opening 18, but also the fine pores. As a result, the transfer film 9 and the separation gel 7 can be closely contacted with each other. It is hence possible to reliably suppress the separated components from diffusing into the buffer solution, and to maintain a stable energization state.

The material of the cover member is, for example, a film-like material, such as a hydrophilic PVDF (Polyvinylidene difluoride) film or a hydrophilic PTFE (Polytetrafluoroethylene) film. The cover member can be attached to the sample separation unit 6, for example, by a method using a adhesive tape or an adhesive, or a method of gripping the sample separation unit 6 and the cover member to be fixedly held together with, e.g., a clip.

The cover member can be impregnated with the separation gel 7, for example, by a method of, after attaching the cover member to the second opening 18 and thereabout, and filling the separation gel 7 into the sample separation unit 6. When a polyacrylamide gel, for example, is used as the separation gel 7, an acrylamide solution before gel polymerization is poured into the sample separation unit 6, to which the cover member has been attached, from the side including the first opening 17. The acrylamide solution is then subjected to the gel polymerization.

In the related art, covering the sample component discharge port with the cover member is not preferable for the reason that the lines of electric force excessively spread while passing through the cover member, and that the sample spreads more widely until teaching the transfer film. However, when the sample separation and adsorption appliance 100 of the present invention is used, there is no problem even when the second opening 18 is covered with the cover member because the lines of electric force are converged by the slit 1, as described later.

In addition, when a certain distance is to be held between the second opening 18 and the transfer film 9 as described later, the provision of the cover member is more preferable in a point of enabling an appropriate distance to be maintained therebetween.

(Slit Structure 8)

The slit structure 8 includes the slit 1 that is formed at a position facing the second opening 18 of the sample separation unit 6. The lines of electric force generated from the negative electrode 2 toward the positive electrode 3 are converged to a convergence point that is given at a center position of the slit 1.

Here, the slit 1 is positioned on the backside of the transfer film 9 (i.e., on the side closer to the positive electrode 3), and the lines of electric force can be narrowed in a region spanning from the separation gel 7 to the slit 1. As a result, the lines of electric force being subjected to the narrowing effect of the slit 1 enter the transfer film 9 that is positioned on the front side of the slit 1 (i.e., on the side closer to the second opening 18). The sample flows along the lines of electric force. Therefore, under an influence of the above-mentioned convergence of the lines of electric force, the sample is adsorbed and held on the transfer film 9 in an enriched state. In other words, the sample can be transferred to the transfer film 9 with high resolution.

In order to adsorb the sample onto the transfer film 9 with higher resolution, it is preferable to arrange the transfer film 9 at a position nearer to the convergence point of the lines of electric force in the slit 1, namely to arrange the slit 1 closer to a rear surface of the transfer film 9. Most preferably, the slit 1 is arranged in a state contacting with the transfer film 9 (i.e., just behind the rear surface of the transfer film 9).

In order to further enhance the effect of converging the lines of electric force, a width of the slit 1 in the y-direction is preferably narrower than that of the second opening 18 in the y-direction. Under such condition, a gradient of an electric field vector toward the convergence point can be increased, and the effect of enriching the sample adsorbed on the transfer film 9 can be further improved. It is to be noted that the lines of electric force are defined as lines interconnecting electric field vectors at individual points.

In order to even further enhance the effect of converging the lines of electric force, the slit structure 8 is preferably made of a material having a low dielectric constant. More preferably, the slit structure 8 is made of an insulating material.

The inside of the slit 1 may be filled with the second buffer solution. Alternatively, the inside of the slit 1 may be filled with an electrically conductive gel, such as an acrylamide gel or an agarose gel, or with a porous film, for example.

When the slit structure 8 is installed in this embodiment, the slit structure 8 can be fixedly mounted, for example, by inserting its end portion into a hole that is formed in the stage 13 at a predetermined position, as illustrated in FIG. 1.

(Transfer Film 9)

The transfer film 9 preferably serves as a sample adsorbing and holding member, which can stably hold the sample, separated in the separation gel 7, for a long term, and which can facilitate an analysis to be performed later. The transfer film 9 is preferably made of a material having high strength and a high sample coupling capability (represented by weight of the sample adsorbable per unit area). When the sample is protein, a PVDF (Polyvinylidene difluoride) film, for example, is suitable as the transfer film 9. The PVDF film is preferably subjected to a hydrophilizing process in advance by employing, e.g., methanol. In addition, a film commonly used so far for adsorption of protein, DNA, and nucleic acids, such as a nitrocellulose film or a nylon film, can also be used.

Samples capable of being separated and adsorbed in the sample separation and adsorption appliance 100 are, though not being restrictive, preparations obtained from biological materials (such as living individuals, biological fluids, cell strains, tissue cultures, and tissue fragments), commercially available reagents, etc. An example of the sample is polypeptide or polynucleotide.

The transfer film 9 runs between the second opening 18 and the slit 1, and it is held at one end by a transfer film storage roll 11 inside the buffer solution tank and at the other end by the moving arm (moving means) 10. The transfer film 9 let out from the transfer film storage roll 11 is conveyed in a direction denoted by an arrow in FIG. 1 with driving of the moving arm 10 when the sample is separated and adsorbed.

Additionally, a guide 12 may be disposed, as required, to guide the transfer film 9 to move along a predetermined path when the transfer film 9 is conveyed. The guide 12 may be provided as a rotatable shaft, for example.

The transfer film storage roll 11 is rotatably mounted to an inner wall of a body of the sample separation and adsorption appliance 100. During the separation and the adsorption of the sample, the transfer film storage roll 11 is preferably positioned at such a height that the transfer film storage roll 11, including the transfer film 9 wound around the same, is entirely immersed in the buffer solution. This aims to prevent drying of the transfer film 9 during the separation and the adsorption of the sample. Moreover, the transfer film storage roll 11 is preferably arranged at a position away from each electrode. This aims to suppress adhesion of bubbles, generated from each electrode, to the transfer film 9. In addition, the transfer film storage roll 11 is made of a material other than materials, e.g., metals, which cause chemical reactions with electricity. Examples of the material of the transfer film storage roll 11 include various types of plastics and glasses.

The sample separation and adsorption appliance 100 may be provided to a user in a state including the transfer film 9 attached in place, or a state not including the transfer film 9, which is attached in place by the user. In any case, the transfer film 9 is brought into a state immersed in the buffer solution.

(Moving Arms 10 and 16)

The moving arm 16 is used to introduce the sample to the first opening 17 of the sample separation unit 6, and it holds a gel strip 14 supported by a support plate 15. Because the gel strip 14 is generally thin and soft, the gel strip 14 is fixed to the support plate 15 formed of, e.g., an acrylic plate, which is in turn held by the moving arm 16, instead of being directly held by the moving arm 16.

Figure 4:
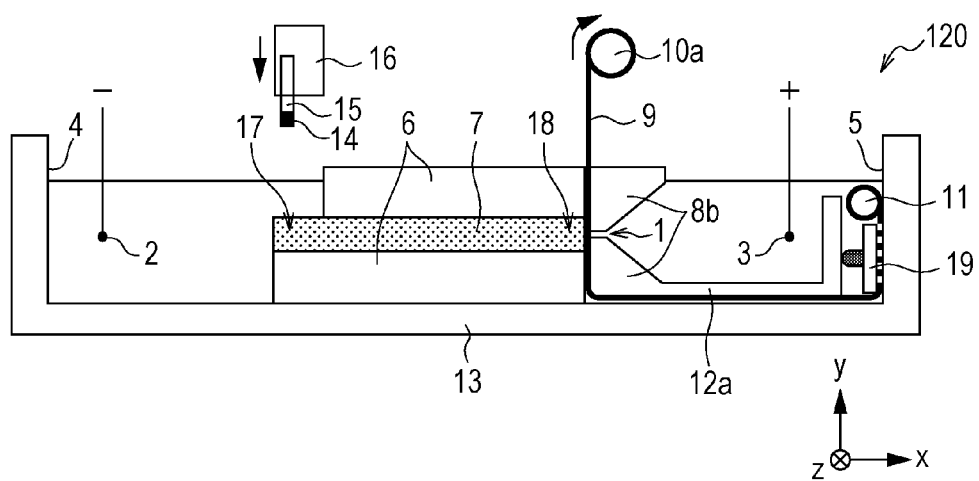
FIG. 4 is a sectional view illustrating a modification of a moving arm in the sample separation and adsorption appliance.

The moving arm 10 is constructed, as illustrated in FIG. 1, to be able to lift up the transfer film 9 in the positive (+) y-direction. The moving arm 10 is not limited to the construction illustrated in FIG. 1, and it may be a transfer film recovery roll 10*a* that winds up the transfer film 9 with rotating operation, as illustrated in FIG. 4. Using the transfer film recovery roll 10*a* is advantageous in not requiring a so large driving range as in the case using the moving arm 10, and in reducing the size of the sample separation and adsorption appliance 100.

While the above-described embodiment employs two arms, i.e., the moving arms 10 and 16, the present invention is not limited to the case using two arms. Only one moving arm may be disposed with omission of the other. In such a case, one moving arm (10 or 16) may be operated to, after introducing the gel strip 14 into the first opening 17, hold and convey the transfer film 9 during the separation and the transfer of the sample.

(Separation and Adsorption of Sample)

A flow of the separation and the adsorption of the sample in the sample separation and adsorption appliance 100 will be described below with reference to FIG. 1.

First, the moving arm 16 holding the gel strip 14 supported by the support plate 15 is moved in a direction denoted by an arrow near the moving arm 16 in FIG. 1 until the gel strip 14 is inserted into or contacted with the first opening 17. Here, the gel strip 14 contains individual components resulting from one-dimensionally separating a sample by isoelectric focusing electrophoresis.

In a state where the gel strip 14 is inserted into or contacted with the first opening 17, a voltage is applied between the negative electrode 2 and the positive electrode 3. Upon the application of the voltage, the individual components contained in the gel strip 14 are separated in the separation gel 7 depending on their molecular weights.

A first dimensional electrophoresis separation unit may be incorporated in the sample separation and adsorption appliance 100 according to this embodiment. Such an arrangement can automate operations including the first dimensional isoelectric focusing electrophoresis separation, the second dimensional electrophoresis separation, and the transfer.

When the first dimensional electrophoresis is not performed, a well (recess) in which the sample is to be filled may be formed in the separation gel 7. After introducing the sample into the well, the sample is fixated using the agarose gel, for example, such that the sample is prevented from flowing out to the first buffer solution tank 4. At that time, the sample may be introduced in a state mixed with the agarose gel to be solidified in the well.

The above-mentioned well is formed in a similar manner to that used in ordinary SDS-PAGE. In more detail, after pouring a gel monomer solution (i.e., a solution prior to gelation with polymerization) into the first opening 17, a comb (usually a comb-like plate having a plurality of projections and recesses formed therein at height (depth) of about 5 mm) is inserted into the first opening 17 before the polymerization of the gel monomer, and the gel monomer is then polymerized. The well is formed by removing the comb after the gelation.

After introducing the sample, the individual components of the sample are separated through electrophoresis by applying a current to flow between the positive electrode 3 and the negative electrode 2. A value of the current flowing between both the electrodes is preferably 50 mA or less and more preferably 20 mA or more and 30 mA or less. With the current value being in the above-mentioned range, the electrophoresis can be carried out at a sufficient rate while generation of heat is suppressed. If a larger current is applied, the electrophoresis cab be finished in a shorter time, but a risk arises in that excessive generation of heat may adversely affect the gel, the sample, or the resolution of electrophoresis separation. However, the excessive generation of heat can be prevented by mounting a high-power cooling device using a Peltier element, for example, at an appropriate location of the sample separation and adsorption appliance 100. In such a case, the current value may be increased to a level of 100 mA or less.

The transfer film 9 is gradually conveyed in the direction denoted by the arrow in FIG. 1 with driving of the moving arm 10 in tune with the progress of electrophoresis in the sample separation unit 6.

Whether the separated components have reached the second opening 18 or not may be determined by previously mixing a stained marker in the sample and then confirming a migration state of the separated components in accordance with a marker position, or by measuring a voltage value with a monitor. The stained marker is preferably BPB (Bromophenol Blue) that is usually employed to confirm the head of migration. Furthermore, an example of the monitor for measuring the voltage value is a voltage monitor (voltage detection means: not illustrated) that monitors a voltage between the negative electrode 2 and the positive electrode 3.

The operation in the case of employing the voltage monitor will be described below. Upon the sample reaching the second opening 18, electrical conductivity reduces at the contact position between the separation gel 7 and the transfer film 9, and a resistance value between both the electrodes increases. Accordingly, the voltage value increases to a large extent. Thus, the fact that the separated components have been discharged from the separation gel 7 and have been transferred to the transfer film 9 can be detected by monitoring the increase of the voltage value. Furthermore, by incorporating a program to monitor the voltage value in the sample separation and adsorption appliance 100, the sample separation and adsorption appliance 100 can be operated to automatically sense the discharge of the components from the separation gel 7 and to start lifting-up of the transfer film 9 with the moving arm 10. Similarly, a lifting speed of the transfer film 9 after the start of adsorption of the components can also be controlled depending on the voltage value or the current value. The lifting speed of the transfer film 9 may be a speed at which the sample can be adsorbed onto the transfer film 9 with satisfactory resolution. Such a speed can be set as appropriate by those skilled in the art. With the above-mentioned control, it is possible to obtain the transfer result with high reproducibility, to avoid wasteful use of the transfer film 9 (i.e., generation of a portion of the transfer film 9 in which the components are not adsorbed), and to reduce the size of the sample separation and adsorption appliance.

According to the above-described steps, the operations from the first or second dimensional electrophoresis to the transfer can be continuously performed in one device.

After the end of adsorption of the sample components, the transfer film 9 is recovered by the moving arm 10 and is subjected to, e.g., staining or an immune reaction. A separation pattern of the components adsorbed onto the transfer film 9 is then detected by employing a fluorescent detector, for example. The fluorescent detector may be incorporated in the sample separation and adsorption appliance 100. Such an arrangement can automate all the steps of electrophoresis, transfer, and detection.

(Other Configurations of Slit Structure 8)

Examples of other configurations capable of being used as the slit structure 8 will be described below with reference to FIGS. 2 to 6.

Figure 2:
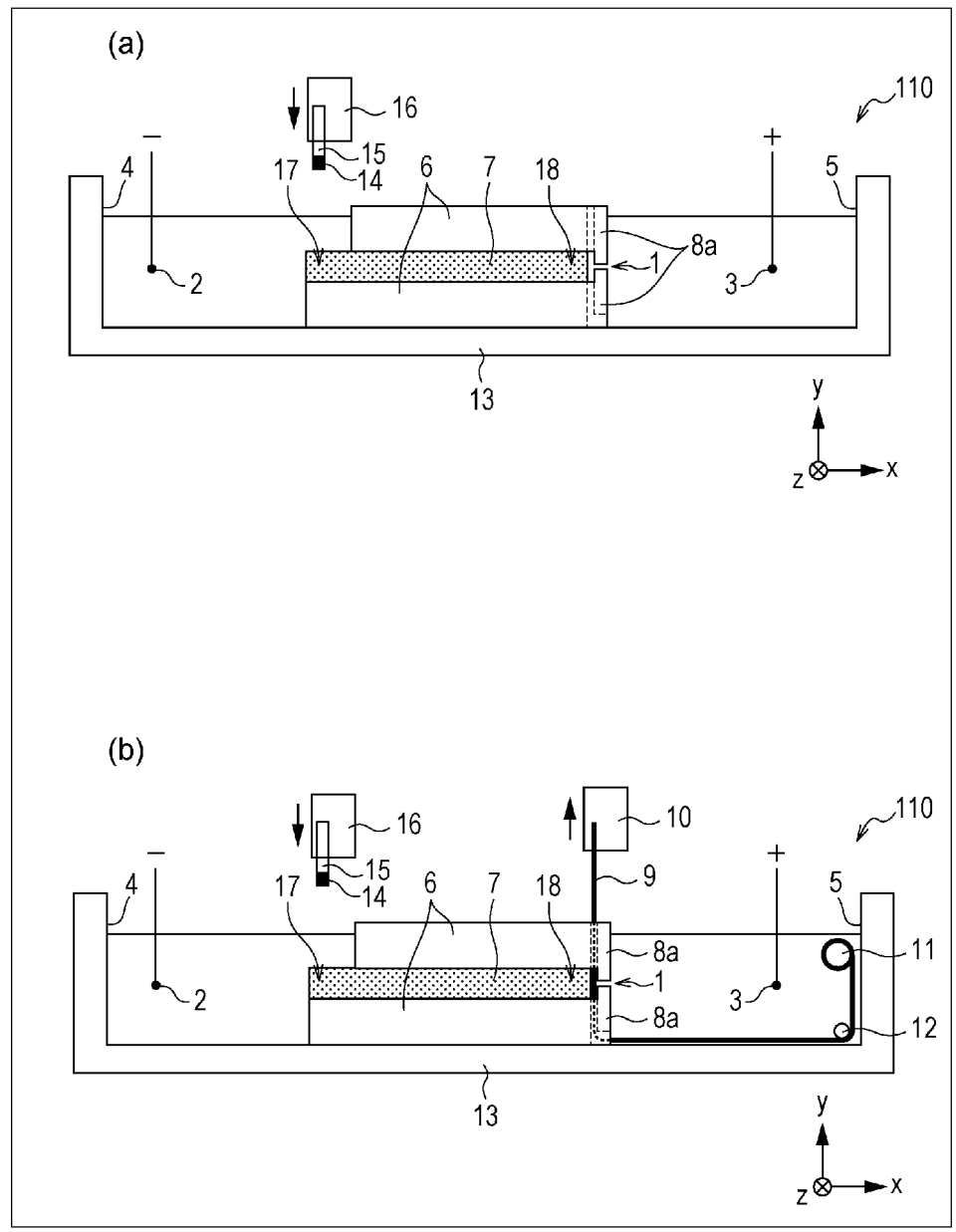
FIGS. 2(a) and 2(b) are sectional views illustrating a modification of a slit structure in the sample separation and adsorption appliance.

FIGS. 2(*a*) and 2(*b*) are sectional views illustrating a sample separation and adsorption appliance 110 provided with a slit structure 8*a*.

As illustrated in FIGS. 2(*a*) and 2(*b*), the slit structure 8*a* may be constructed integrally with the sample separation unit 6. The slit structure 8*a* includes the slit 1 formed therein, and further includes a path for insertion of the transfer film 9 as denoted by dotted lines in FIG. 2(*a*). The transfer film 9 is installed, as illustrated in FIG. 2(*b*), by inserting the transfer film 9 into the insertion path.

The slit structure 8*a* can be appropriately modified, for example, such that a portion of the sample separation unit 6, which constitutes the slit structure 8*a*, is constructed to be able to open and close in the x-direction for easier insertion of the transfer film 9.

The configuration illustrated in FIGS. 2(*a*) and 2(*b*) has the advantages that fine adjustment of the position of the slit 1 relative to the second opening 18 is no longer required, and that the number of assembly steps necessary for preparing the sample separation and adsorption appliance 110 is reduced.

Figure 3:
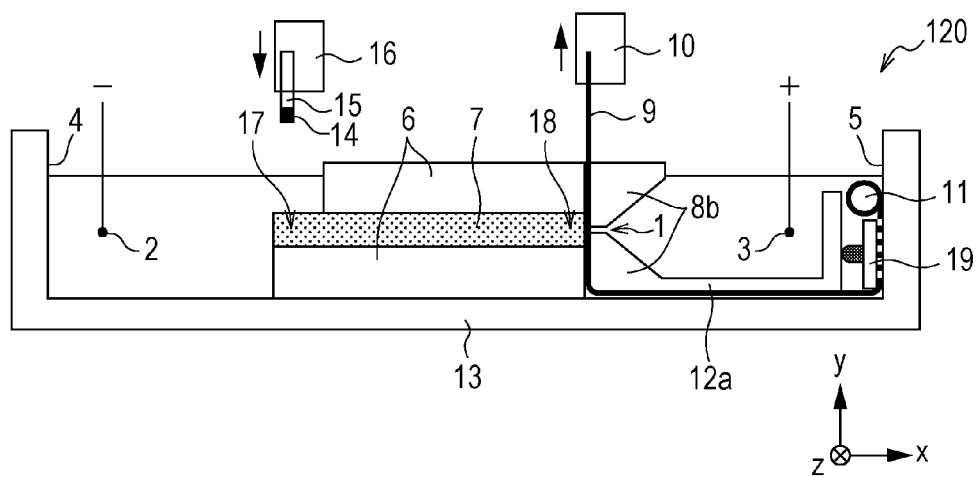
FIG. 3 is a sectional view illustrating a modification of the slit structure in the sample separation and adsorption appliance.

FIGS. 3 and 4 are each a sectional view of a sample separation and adsorption appliance 120 including a slit structure 8b.

As illustrated in FIGS. 3 and 4, a part of the slit structure 8b extends along a bottom surface of the second buffer solution tank 5 nearby until reaching a lateral surface thereof, and includes an extended portion 12a that forms a double bottom of the second buffer solution tank 5. A jig, e.g., a plunger 19, is set in operative relation with respect to the extended portion 12a such that the slit structure 8b may be pressed toward the second opening 18. That arrangement enables the slit 1 and the transfer film 9 to be satisfactorily contacted with each other.

The transfer film 9 may be conveyed to pass between the extended portion 12a forming the double bottom of the second buffer solution tank 5 and the stage 13.

Furthermore, a surface of the slit structure 8b on the side closer to the second opening 18 is inclined to spread toward opposite sides in the y-direction symmetrically about the slit 1 being a center. With such a configuration, because the buffer solution having a high dielectric constant is surely maintained behind the slit 1 (i.e., on the side closer to the positive electrode 3), it is possible to reduce resistance that is generated to introduce (converge) the lines of electric force into a slit space, which is surrounded by the slit structure 8b having a low dielectric constant.

The sample separation and adsorption appliance 120 illustrated in FIG. 4 includes the transfer film recovery roll 10a, described above, instead of the moving arm 10.

Figure 5:
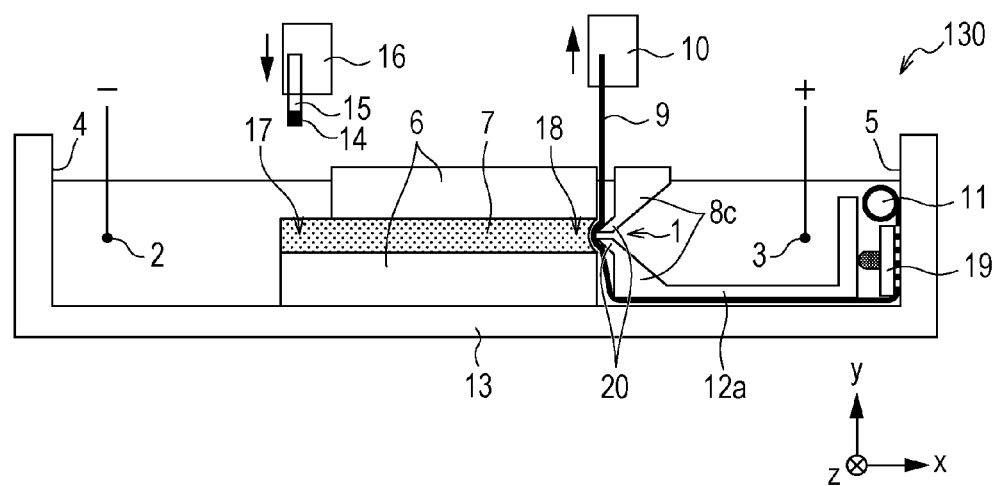
FIG. 5 is a sectional view illustrating a modification of the slit structure in the sample separation and adsorption appliance.
Figure 6:
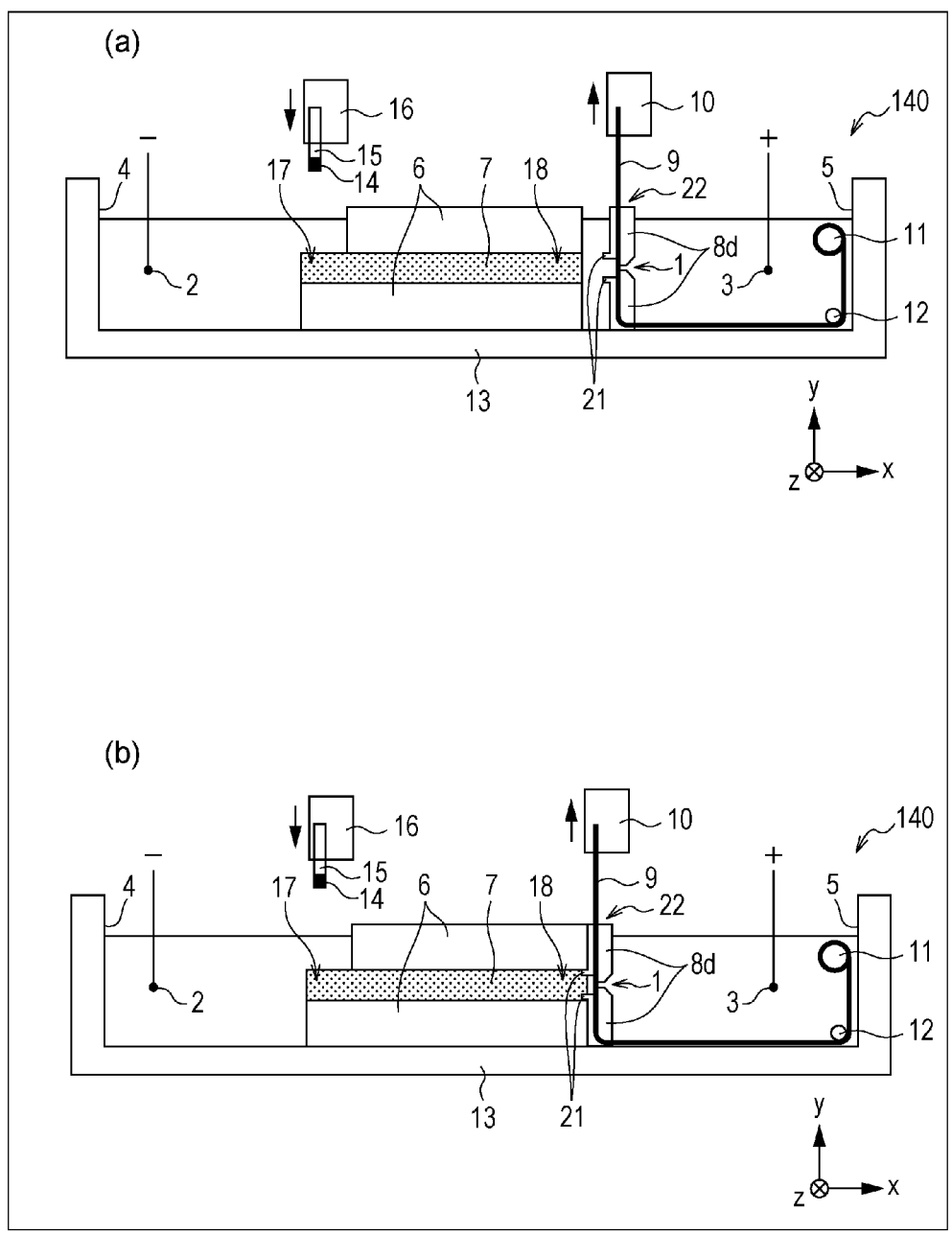
FIGS. 6(a) and 6(b) are sectional views illustrating a modification of the slit structure in the sample separation and adsorption appliance.

FIG. 5 is a sectional view of a sample separation and adsorption appliance 130 including a slit structure 8c.

As illustrated in FIG. 5, the slit structure 8c includes two projections 20 that are formed by partly projecting the slit structure 8c in a beak-like shape toward the second opening 18, and the slit 1 is formed between the projections 20. The projections 20 have distal ends entering the sample separation unit 6 through the second opening 18. With such a configuration, a center position of the slit 1 and a center position of the second opening 18 can be easily located on the same plane with higher accuracy, and adhesion between the separation gel 7 and the slit structure 8c, i.e., between the separation gel 7 and the transfer film 9, can be increased.

Here, the projections 20 of the slit structure 8c are at least contacted with the separation gel 7 while the transfer film 9 is interposed therebetween. Preferably, the projections 20 are pushed into the separation gel 7 together with the transfer film 9. From that point of view, the sample separation and adsorption appliance 130 preferably includes a mean for moving the slit structure 8c toward the sample separation unit 6 from the side closer to the second buffer solution tank 5. Such a means may be realized, for example, by forming a portion of the slit structure 8c to constitute the double bottom of the second buffer solution tank 5 and then pressing the slit structure 8c toward the second opening 18 with, e.g., the plunger 19 as illustrated in FIG. 5, or by pushing the slit structure 8c to a predetermined position with, e.g., a spring or a rivet, and then fixing the slit structure 8c.

FIGS. 6(a) and 6(b) are each a sectional view of a sample separation and adsorption appliance 140 including a slit structure 8d.

As illustrated in FIGS. 6(a) and 6(b), the slit structure 8d includes a projection 21 projecting from a periphery of the slit 1 and entering the sample separation unit 6 through the second opening 18, and a holding portion 22 that holds the transfer film 9. It is to be noted that FIG. 6(a) represents a state before the projection 21 is inserted, and FIG. 6(b) represents a state after the projection 21 has been inserted.

As illustrated in FIG. 6(b), the projection 21 pushes the separation gel 7 in the sample separation unit 6 such that the separation gel 7 is moved into a space surrounded by the front side (i.e., the side closer to the second opening 18) of the transfer film 9 and the projection 21, and that the separation gel 7 is filled in the above-mentioned space in close contact state. Furthermore, the holding portion 22 includes a space formed inside the slit structure 8d between the projection 21 and the slit 1, for example, the space allowing the transfer film 9 to pass therethrough. The holding portion 22 may be constituted to be able to open and close in the x-direction and to fixedly hold the transfer film 9 as in the configuration of FIG. 2(b).

Stated in another way, the slit structure 8d can linearly lift up the transfer film 9 while the adhesion between the separation gel 7 and the transfer film 9 is increased in comparison with that in the case using the slit structure 8c. Moreover, as in the case using the slit structure 8c, the center position of the slit 1 and the center position of the second opening 18 can be easily located on the same plane with higher accuracy.

In addition, the sample separation and adsorption appliance 140 also preferably includes a means capable of pushing and fixing the slit structure 8d to the predetermined position with, e.g., a spring or a rivet.

Second Embodiment

Figure 15:
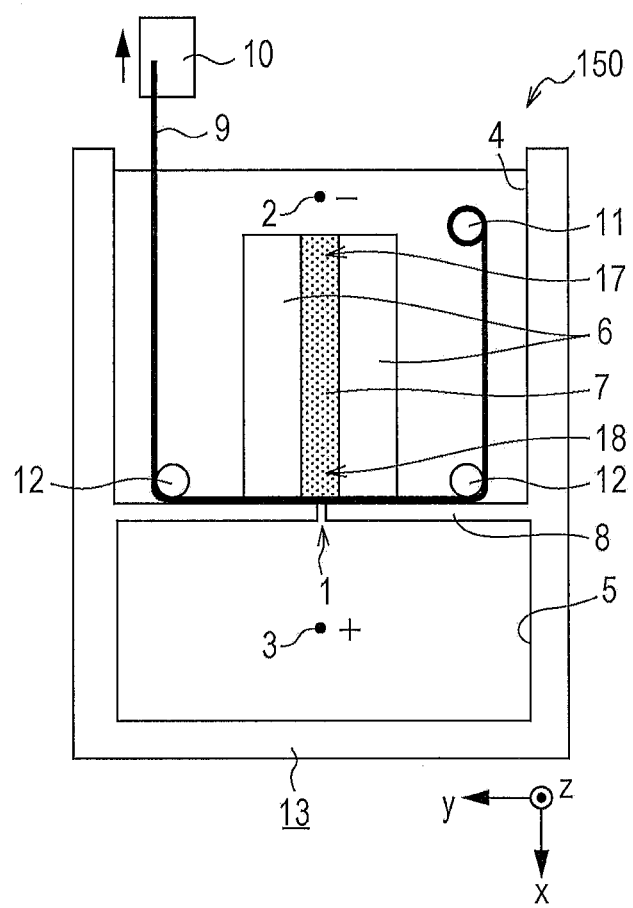
FIG. 15 is a sectional view illustrating a basic structure of a sample separation and adsorption appliance according to another embodiment of the present invention.

A second embodiment of the present invention will be described below with reference to FIG. 15. FIG. 15 is a sectional view of a sample separation and adsorption appliance 150.

The second embodiment is different from the above-described first embodiment primarily in that the sample separation and adsorption appliance 150 is a vertically-installed device.

Accordingly, the following description is made primarily with respect to such a different point. It is to be noted that constituent elements having functions corresponding to those of the constituent elements in the first embodiment are denoted by the same reference signs.

In the sample separation and adsorption appliance 150, as illustrated in FIG. 15, the stage 13 is constituted as two divided tanks by mounting the sample separation unit 6 and a slit structure 8e within the stage 13, thus forming the first buffer solution tank 4 and the second buffer solution tank 5. The slit structure 8e may be constituted integrally with a stage body.

The transfer film storage roll 11 is arranged in the first buffer solution tank 4, and the transfer film 9 is withdrawn upward.

According to the second embodiment, as in the above-described first embodiment, the sample adsorption with high resolution can be realized in the mode of continuously performing the process from the second dimensional electrophoresis to the transfer.

Figure 16:
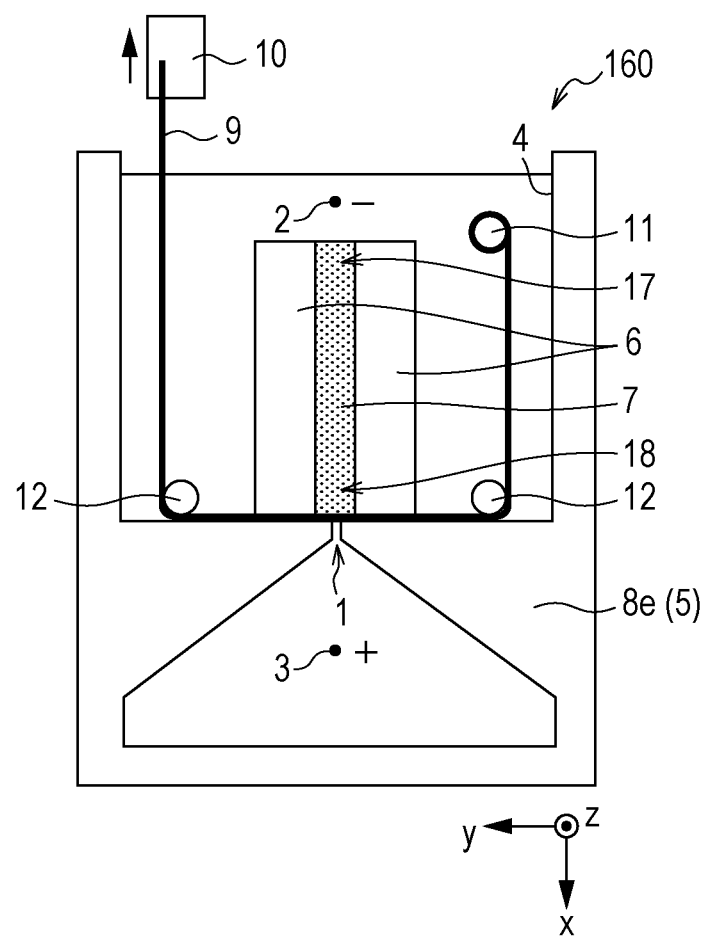
FIG. 16 is a sectional view illustrating a modification of a slit in the sample separation and adsorption appliance.

FIG. 16 is a sectional view of a sample separation and adsorption appliance 160 according to a modification. In the sample separation and adsorption appliance 160, a slit structure 8f is constituted integrally with the stage 13 and is formed symmetrically with respect to a center plane (xz-plane) of the slit 1. Such a configuration can reduce resistance that is generated to make the lines of electric force converged into the slit 1.

(Sum-Up)

As described above, the present invention provides a sample separation and adsorption appliance for separating a sample in a separation medium by applying a current to the separation medium through a buffer solution, and for adsorbing the separated sample onto a sample adsorption member from the separation medium, wherein the sample separation and adsorption appliance includes a first electrode, a second electrode, a sample separation unit that has a first opening opened to a side facing the first electrode and a second opening opened to a side facing the second electrode, the sample separation unit containing the separation medium, and a slit structure including a slit at a position facing the second opening, wherein the sample adsorption member is arranged between the second opening and the slit.

With the features described above, since the sample separation unit containing the separation medium has the first opening and the second opening, the first electrode and the second electrode are electrically connected to each other through the buffer solution, the separation medium, and the sample adsorption member upon application of a voltage between the first electrode and the second electrode. Furthermore, the slit arranged at the position facing the second opening acts to converge the lines of electric force, which advance from the first electrode toward the second electrode.

Upon the application of the voltage between the first electrode and the second electrode, the sample is caused to migrate through the separation medium and is separated into plural components. The separated sample components flow along the lines of electric force even after being discharged from the second opening, and they are adsorbed onto the sample adsorption member.

Here, since the sample adsorption member is arranged between the second opening and the slit, the lines of electric force pass through the sample adsorption member while being converged toward the slit from the second opening. In other words, the sample flowing along the lines of electric force is converged in a process during which the sample is discharged from the second opening and is adsorbed onto the sample adsorption member.

According to the features described above, therefore, it is possible to suppress spreading of sample adsorption with respect to the sample adsorption member, and to realize the sample adsorption with higher resolution.

In the case of adsorbing the separated sample onto the sample adsorption member from the separation medium, a sample separation pattern can be obtained by moving the sample adsorption member in a second direction perpendicular to a first direction that is specified by the first electrode and the second electrode.

Moreover, according to the features described above, the second dimensional electrophoresis and the transfer can be continuously performed by setting, as the sample, a separation medium that has been subjected to the first dimensional electrophoresis.

In the sample separation and adsorption appliance according to the present invention, preferably, a width of the slit is narrower than a width of the second opening in a second direction perpendicular to a first direction that is specified by the first electrode and the second electrode.

According to the feature described above, the slit acts to converge the lines of electric force to its width narrower than that of the second opening. Therefore, the sample discharged from the second opening can be converged to a zone narrower than the width of the second opening, and sample adsorption can be realized with higher resolution.

In the sample separation and adsorption appliance according to the present invention, preferably, the slit structure is made of an insulating material.

In the sample separation and adsorption appliance according to the present invention, preferably, the slit structure is made of a material having a dielectric constant of 5.0 or less.

By forming the slit in the slit structure made of the above-mentioned material, the slit can more effectively converge the lines of electric force. As a result, the sample adsorption can be realized with even higher resolution.

In the sample separation and adsorption appliance according to the present invention, preferably, the sample adsorption member is arranged in contact with the slit, and a distance between the second opening and the slit in the first direction is 300 μm or more and 4000 μm or less.

According to the features described above, a proper distance necessary for convergence of the sample is secured between the second opening and the slit. If the above-mentioned distance is shorter than 300 μm, the sample would reach the sample adsorption member before being converged sufficiently. On the other hand, if the above-mentioned distance is longer than 4000 μm, convergence force generated by the slit would not sufficiently exert up to the vicinity of the second opening, and the sample discharged from the second opening would be subjected to diffusion force that is greater than the convergence force.

Furthermore, according to the features described above, since the sample adsorption member is arranged in contact with the slit, the sample is adsorbed at a position where the sample is converged maximally. Accordingly, the sample adsorption can be realized with even higher resolution.

In the sample separation and adsorption appliance according to the present invention, when the second opening and the sample adsorption member are not contacted with each other, an electrically conductive medium allowing the sample to pass therethrough is preferably interposed between the second opening and the sample adsorption member.

According to the features described above, the sample is avoided from diffusing into the buffer solution, and the sample can be reliably adsorbed onto the sample adsorption member.

In the sample separation and adsorption appliance according to the present invention, preferably, the slit structure includes a projected portion in shape having projections toward the second opening with the slit being formed between the projections, and at least a part of the projected portion is held in a state entering the sample separation unit through the second opening together with the sample adsorption member and contacting with the separation medium while the sample adsorption member is interposed therebetween.

According to the features described above, a center position of the slit and a center position of the second opening can be easily aligned with each other in the second direction. By setting both the center positions to be aligned with each other, accuracy of the sample adsorption can be improved without causing a deviation of the convergence force generated by the slit. Moreover, since the separation medium and the sample adsorption member are closely contacted with each other, the sample can be reliably adsorbed onto the sample adsorption member.

In the sample separation and adsorption appliance according to the present invention, preferably, the slit structure includes:

a projected portion having a shape projecting toward the second opening from a periphery of the slit and entering the sample separation unit through the second opening, and a holding member that holds the sample adsorption member between the projected portion and the slit.

According to the features described above, since the separation medium is present in a space surrounded by the projection and the sample adsorption member and adhesion between the separation medium and the sample adsorption member is increased, the sample can be adsorbed with higher reliability. Moreover, since the center position of the slit and the center position of the second opening can be easily aligned with each other in the second direction, the accuracy of the sample adsorption can be improved without causing a deviation of the convergence force generated by the slit.

In addition, according to the features described above, since the holding portion holds the sample adsorption member, the sample adsorption member can be linearly lifted up, while the adhesion between the separation medium and the sample adsorption member is increased, in the case of moving the sample adsorption member during the sample adsorption. As a result, a sample separation pattern can be obtained with higher accuracy.

The sample separation and adsorption appliance according to the present invention, preferably, further comprises a first buffer solution tank in which the first electrode is arranged, and a second buffer solution tank in which the second electrode is arranged, wherein the slit structure is constituted integrally with the second buffer solution tank, and at least a portion of the second buffer solution tank, the portion including the slit structure, is constituted symmetrically with respect to a plane that passes a center of the slit in the above-mentioned second direction, and that is perpendicular to the second direction.

According to the features described above, since the slit structure and the second buffer solution tank are integral with each other, the preparation of the sample separation and adsorption appliance can be facilitated. Moreover, since at least the portion of the second buffer solution tank has the symmetric shape, it is possible to eliminate even a slight factor that makes a flow of the sample anisotropic, and to further improve the accuracy of the sample adsorption.

In the sample separation and adsorption appliance according to the present invention, preferably, the slit structure is constituted integrally with the sample separation at a side of the sample separation unit closer to the second opening.

According to the feature described above, since fine adjustment, etc. necessary for positioning of the slit relative to the second opening is no longer needed, and the preparation of the sample separation and adsorption appliance can be facilitated.

In the sample separation and adsorption appliance according to the present invention, preferably, the first electrode, the first opening, the second opening, and the second electrode are arranged substantially on one linear line.

According to the feature described above, since the lines of electric force flow perpendicularly to the sample adsorption member near the second opening, the sample discharged from the second opening is adsorbed in a direction perpendicular to the sample adsorption member. As a result, the accuracy of the sample adsorption can be further improved.

The sample separation and adsorption appliance according to the present invention, preferably, further comprises a guide to specify a path along which the sample adsorption member is to be moved.

According to the feature described above, since the sample adsorption member is moved along the predetermined path, the sample adsorption member can smoothly move without interfering with other members, etc.

The sample separation and adsorption appliance according to the present invention, preferably, further comprises moving means for moving the sample adsorption member at the position facing the second opening in the above-mentioned second direction.

According to the feature described above, since the sample adsorption member can be automatically moved in the second direction, a sample separation pattern can be obtained with higher accuracy.

The sample separation and adsorption appliance according to the present invention, preferably, further comprises voltage detection means for measuring a voltage between the first electrode and the second electrode, wherein the moving means starts the movement of the sample adsorption member in accordance with the voltage detected by the voltage detection means.

According to the features described above, since the sample adsorption member can be moved at the same time as the start of the adsorption, the result can be obtained with good reproducibility, and wasteful use of the sample adsorption member can be avoided.

EXAMPLE

The present invention will be described in detail below in connection with EXAMPLE, but the present invention is not limited to the following EXAMPLE.

(Particle Orbit Simulations Using Sample Separation and Adsorption Appliance 120)

Detailed studies in relation to the slit 1 are described according to the results of particle orbit simulations.

Figure 7:
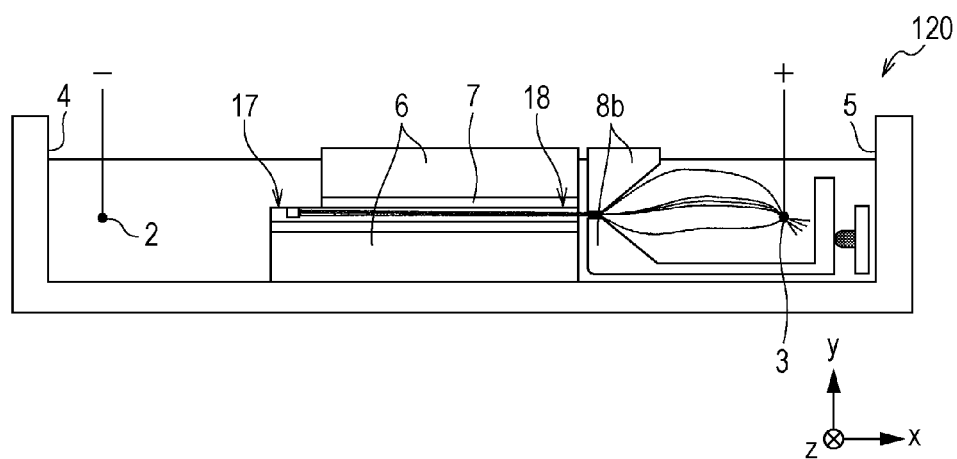
FIG. 7 illustrates a configuration of a model for the sample separation and adsorption appliance, the model being used in particle orbit simulations.

The sample separation and adsorption appliance 120 illustrated in FIG. 7 was used as a model for the sample separation and adsorption appliance. The sample separation and adsorption appliance 120 including the slit structure 8b was set such that the sample separation unit 6 was made of glass, and that the slit structure 8b and the stage 13 were each formed of an acrylic plate. Furthermore, the width of the second opening 18 in the y-direction was fixedly set to 1.2 mm (=1200 µm). The electrodes were each made of platinum, and a voltage of 200 V was applied between the electrodes.

On the basis of the above-mentioned setting, migration behaviors of lysozyme protein (molecular weight of 14037Da and isoelectric point of 11.1), which was a model sample, with the first opening 17 being a start point were observed while conditions related to the slit 1 were changed.

<Width of Slit 1>

First, the particle orbit simulation was carried out by changing one condition of the slit 1, i.e., the width of the slit 1 in the y-direction, to be reduced gradually from 1.2 mm. FIG. 8 and FIGS. 9(a) to 9(d) illustrate the simulation results.

Figure 8:
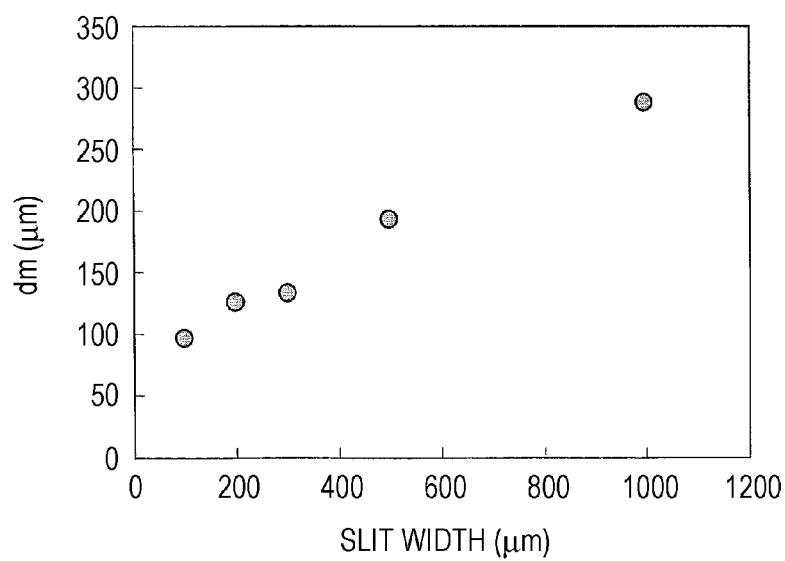
FIG. 8 is a graph plotting spreading of the lines of electric force at a center of a sample adsorption member when a slit width is changed.

FIG. 8 is a graph of the result of plotting, in accordance with the particle orbit simulation, spreading (range (dm) in the y-direction) of the lines of electric force at a center of the transfer film 9 (i.e., a midpoint of its thickness in the x-direction). FIGS. 9(a) to 9(d) are diagrams illustrating the simulation results near the second opening 18. The width of the slit in the y-direction is 0.1 mm in FIG. 9(a), 0.2 mm in FIG. 9(b), 0.5 mm in FIG. 9(c), and 1.0 mm in FIG. 9(d).

Figure 9:
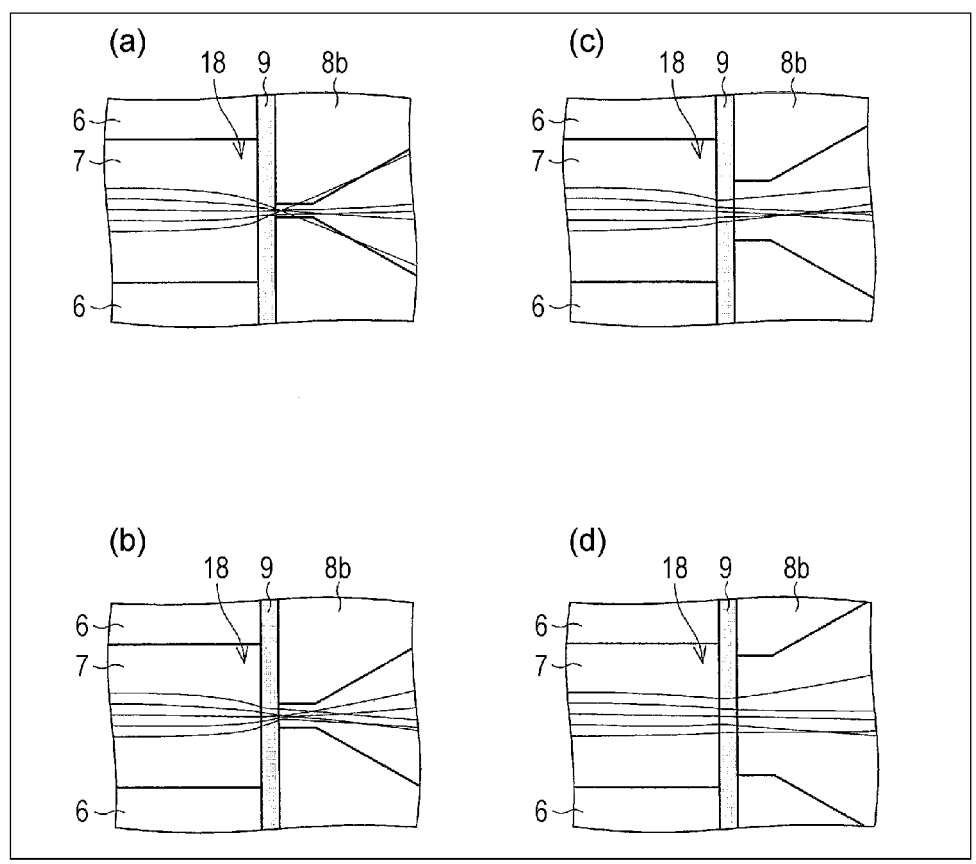
FIGS. 9(a) to 9(d) each represent spreading of the lines of electric force when the slit width is changed.

As illustrated in FIGS. 8 and 9, the narrower the width of the slit 1 in the y-direction, the smaller was dm. In other words, it can be seen that as the width of the slit 1 in the y-direction reduces, the sample is adsorbed onto the transfer film 9 with higher resolution. Accordingly, the objective resolution can be obtained by specifying the width of the slit 1 in the y-direction.

The width of the slit 1 in the x-direction is preferably as small as possible within such a range that the strength of the slit 1 can be maintained. The reason is that, as the width of the slit 1 in the x-direction reduces, resistance generated with electricity flowing through a narrow space can be held smaller.

<Dielectric Constant of Material of Slit Structure 8*b*>

Figure 10:
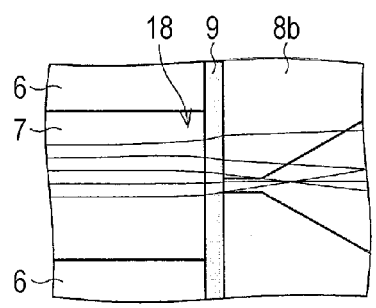
FIGS. 10(a) to 10(c) each represent spreading of the lines of electric force when a material of the slit structure is changed.
Figure 10:
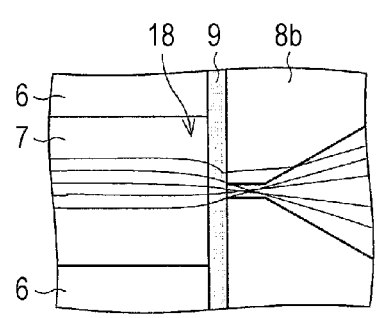
Figure 10:
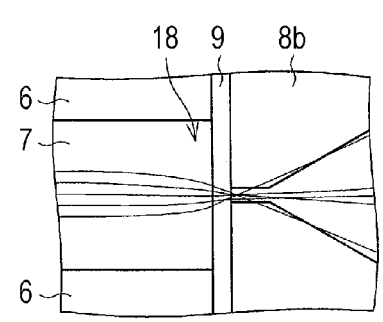

Next, the particle orbit simulation was carried out by changing another condition of the slit 1, i.e., the dielectric constant of the material of the slit structure 8*b*. FIGS. 10(*a*) to 10(*c*) illustrate the simulation results.

FIG. 10 is a diagram illustrating the simulation result near the second opening 18. The dielectric constant of the material of the slit structure 8*b* was 10 in FIG. 10(*a*) and 5 in FIG. 10(*b*), whereas the material of the slit structure 8*b* in FIG. 10(*c*) was an insulating material.

As seen from FIGS. 10(*a*) to 10(*c*), the lines of electric force are more apt to converge into the slit 1 when the slit structure 8*b* is made of a material having a lower dielectric constant, and the lines of electric force are converged maximally when the slit structure 8*b* is made of an insulating material. Furthermore, using the material having a lower dielectric constant to form the slit structure 8*b* reduces a possibility that the lines of electric force advance through a wall portion of the slit structure 8*b* and the transfer film 9, which are positioned other than a gap to form the slit 1. More specifically, the dm value at the dielectric constant of 10 is 443.1 μm (FIG. 10(*a*)), the dm value at the dielectric constant of 5 is 267.1 μm (FIG. 10(*b*)), and the dm value in the case of employing insulating material is 96.7 μm (FIG. 10(*c*)).

Thus, it is understood that the sample can be adsorbed onto the transfer film 9 with higher resolution by using a material having a lower dielectric constant (preferably 5.0 or less), more preferably an insulating material, to form the slit structure 8*b*.

As is apparent from the above description, the material of the slit structure 8*b* is desirably made of a material that can be machined to provide the slit 1 in a thickness as thin as possible, and that is an insulator (or a substance having a low dielectric constant). Examples of such a material include acrylic (dielectric constant of 2.7 to 4.5), polycarbonate (dielectric constant of 2.9 to 3.0), and fluorine resins such as 4-fluoroethylene (PTFE) (dielectric constant of 2), perfluoroalkoxy alkane (PFA) (dielectric constant of 2.1), and polychlorotrifluoroethylene (PCTFE) (dielectric constant of 2.3 to 2.8).

<Distance Between Slit 1 and Second Opening 18>

Figure 11:
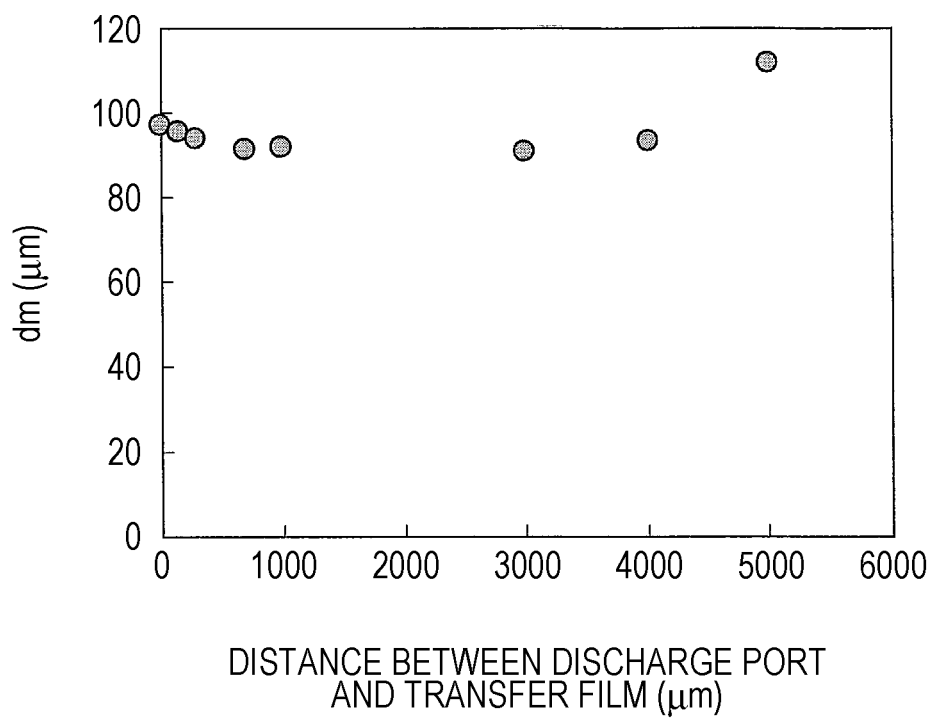
FIG. 11 is a graph plotting spreading of the lines of electric force at the center of the sample adsorption member when a distance between a second opening and a slit is changed.
Figure 12:
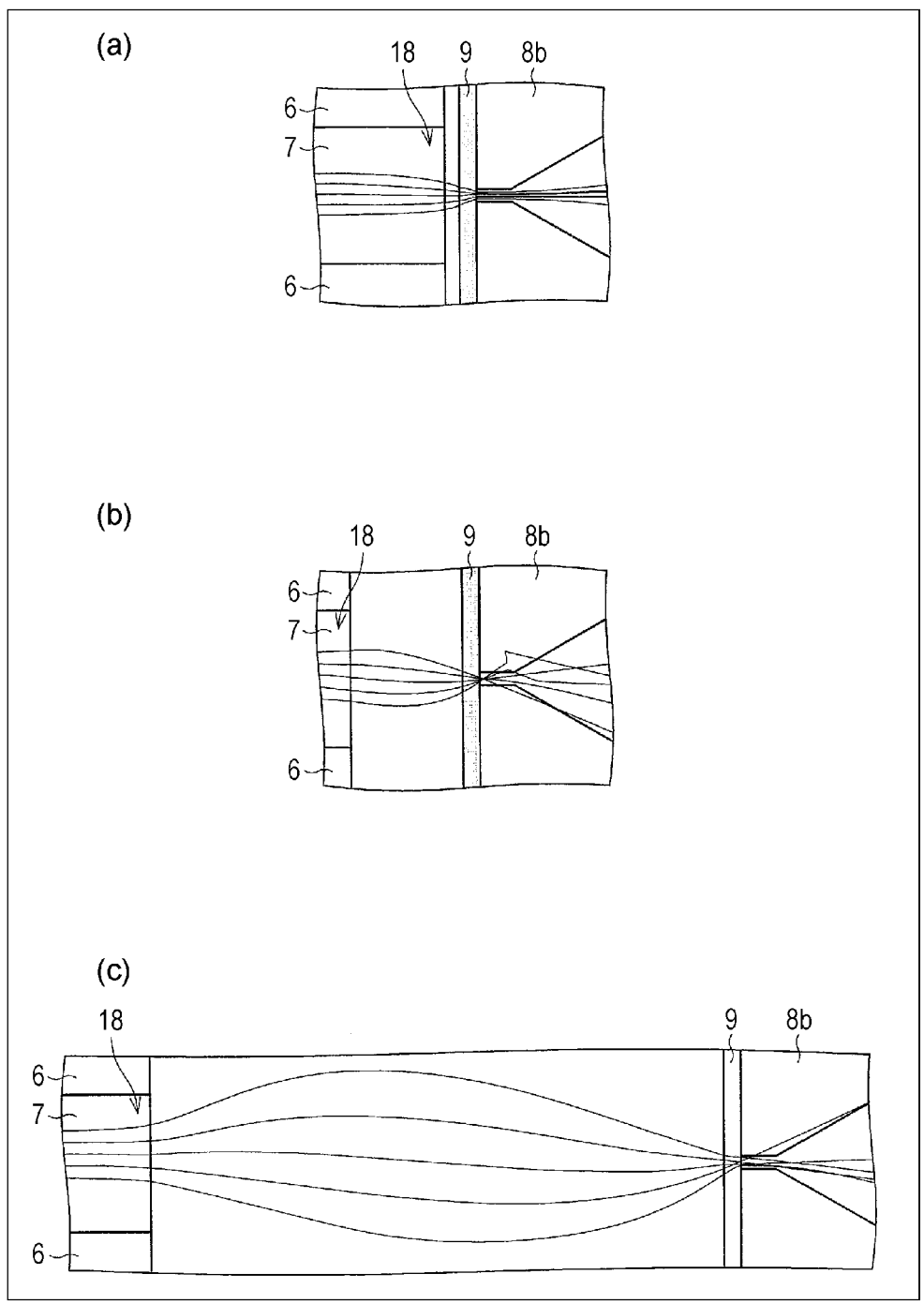
FIGS. 12(a) to 12(c) each represent spreading of the lines of electric force when the distance between the second opening and the slit is changed.

Next, the particle orbit simulation was carried out by changing still another condition of the slit 1, i.e., the distance between the slit 1 and the second opening 18. FIGS. 11 and 12 illustrate the simulation results. Because the transfer film 9 and the slit 1 were always held in contact with each other in the case of changing the above-mentioned distance, the distance between the second opening 18 and the transfer film 9 was also changed with the change of the distance between the slit 1 and the second opening 18.

FIG. 11 is a graph obtained by simulating an influence of the distance between the second opening 18 and the slit 1 upon the dm value, and by plotting the simulation result. In the graph of FIG. 11, the horizontal axis represents the distance between the second opening 18 and the transfer film 9. FIGS. 12(*a*) to 12(*c*) are diagrams illustrating the simulation results when the above-mentioned distance is changed. The above-mentioned distance is 140 μm in FIG. 12(*a*), 1000 μm in FIG. 12(*b*), and 5000 μm in FIG. 12(*c*).

The following description is made with reference to FIGS. 11 and 12. As seen from FIG. 11, as the distance between the second opening 18 and the transfer film 9 increases from 0 μm (i.e., a state where the second opening 18 and the transfer film 9 are contacted with each other) to 700 μm, the dm value reduces and higher resolution is resulted. The reason is that, as illustrated in FIG. 12(*a*), a distance necessary for the sample to converge is secured between the second opening 18 and the slit 1, whereby the convergence force of the slit 1 contributes to the effect of increasing the resolution.

On the other hand, when the distance between the second opening 18 and the transfer film 9 increases from 700 μm, the convergence effect of the slit 1 exerted on the sample immediately after being discharged from the second opening 18 weakens, and force acting to diffuse the sample immediately after being discharged increases.

When the above-mentioned distance is in the range of 700 μm or more to less than 3000 μm, an equilibrium state where the dm value is settled at a minimum value continues under balance between the force acting to diffuse the sample and the convergence force of the slit 1, the latter including a contribution due to the above-mentioned distance. In that range, as illustrated in FIG. 12(*b*), the sample immediately after being discharged from the second opening 18 tends to spread temporarily, and thereafter the sample is narrowed under the increasing effect of the convergence force of the slit 1 as the sample comes closer to the slit 1.

When the distance between the second opening 18 and the transfer film 9 becomes 3000 μm or more, the dm value increases gradually, as illustrated in FIG. 12(*c*), because the diffusion force exerted on the sample discharged from the second opening 18 increases, thus causing the sample to diffuse over a wider range.

To sum up the above discussion, it is understood from FIG. 11 that when the distance between the second opening 18 and the transfer film 9 is 300 μm or more and 4000 μm or less, the dm value is lower than that in the case where the second opening 18 and the transfer film 9 are in contact with each other. Hence higher resolution is obtained.

However, if the medium present between the second opening 18 and the slit 1 is the buffer solution, the sample would tend to diffuse. Accordingly, an electrically conductive medium, e.g., a gel, allowing the sample to pass therethrough is preferably interposed between the second opening 18 and the slit 1. Such an electrically conductive medium is, for example, the cover member described above in the paragraphs subtitled (Sample Separation Unit 6).

It is to be noted that the above-described preferred conditions, etc. regarding the slit structure 8*b* are all similarly applied to the other slit structures.

(Particle Orbit Simulation Using Sample Separation and Adsorption Appliance 130)

Detailed studies in relation to the slit structure 8*c* in which the slit 1 is pushed into the sample separation unit 6 are described below according to the result of a particle orbit simulation.

Figure 13:
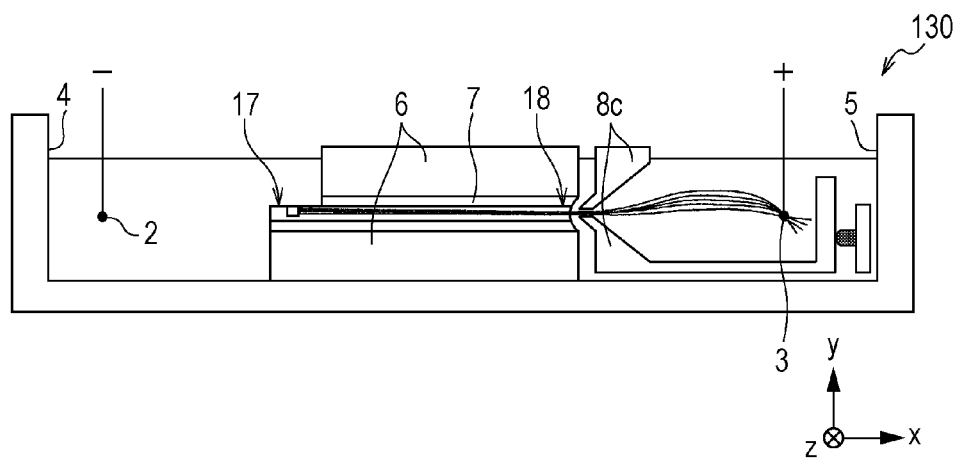
FIG. 13 illustrates a configuration of a model for the sample separation and adsorption appliance, the model being used in particle orbit simulations.

The sample separation and adsorption appliance 130 illustrated in FIG. 13 was used as a model for the sample separation and adsorption appliance. Other basic settings were the same as those in the above-described simulations. Furthermore, the sample separation and adsorption appliance 120 having the structure not pushing the slit 1 into the sample separation unit 6 was used as a model for comparative reference.

Figure 14:
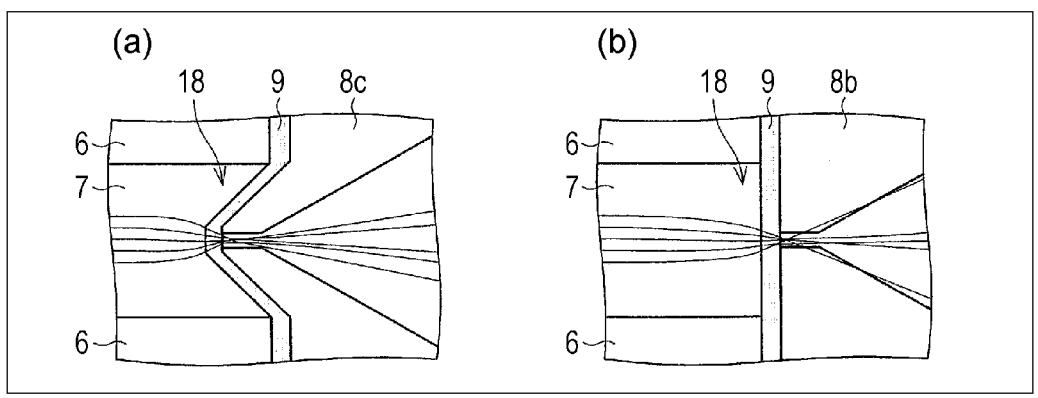
FIG. 14(a) is an enlarged view of the vicinity of the second opening, the view illustrating the result of the particle orbit simulation obtained with a configuration in which the slit is in form protruding into the second opening.
FIG. 14(b) is an enlarged view illustrating the result obtained with a configuration in which the slit is in form not protruding into the second opening.

FIG. 14(*a*) is a diagram illustrating the simulation result near the second opening 18 of the sample separation and adsorption appliance 130. FIG. 14(*b*) is a diagram illustrating the simulation result near the second opening 18 of the sample separation and adsorption appliance 120 as the comparative reference.

In FIG. 14(a), the dm value is 114.2 µm, and in FIG. 14(b), the dm value is 96.7 µm. Stated in another way, in the structure pushing the slit 1 into the sample separation unit 6, since the separation gel is positioned above and below the slit 1 (in the y-direction), the lines of electric force are subjected to force acting to diverge them in the y-direction, and the resolution degrades slightly (namely, the dm value increases slightly).

However, the above-mentioned increase of the dm value in the structure pushing the slit is such an extent as capable of being sufficiently compensated for by changing the width of the slit 1 and the material of the slit structure 8c. Thus, the increase of the dm value is not so significant in consideration of the above-described advantages of the slit structure 8c.

(Particle Orbit Simulation in Comparative Example)

As Comparative Example, the particle orbit simulation was carried out using a sample separation and adsorption appliance 200 not including the slit structure.

Figure 17:
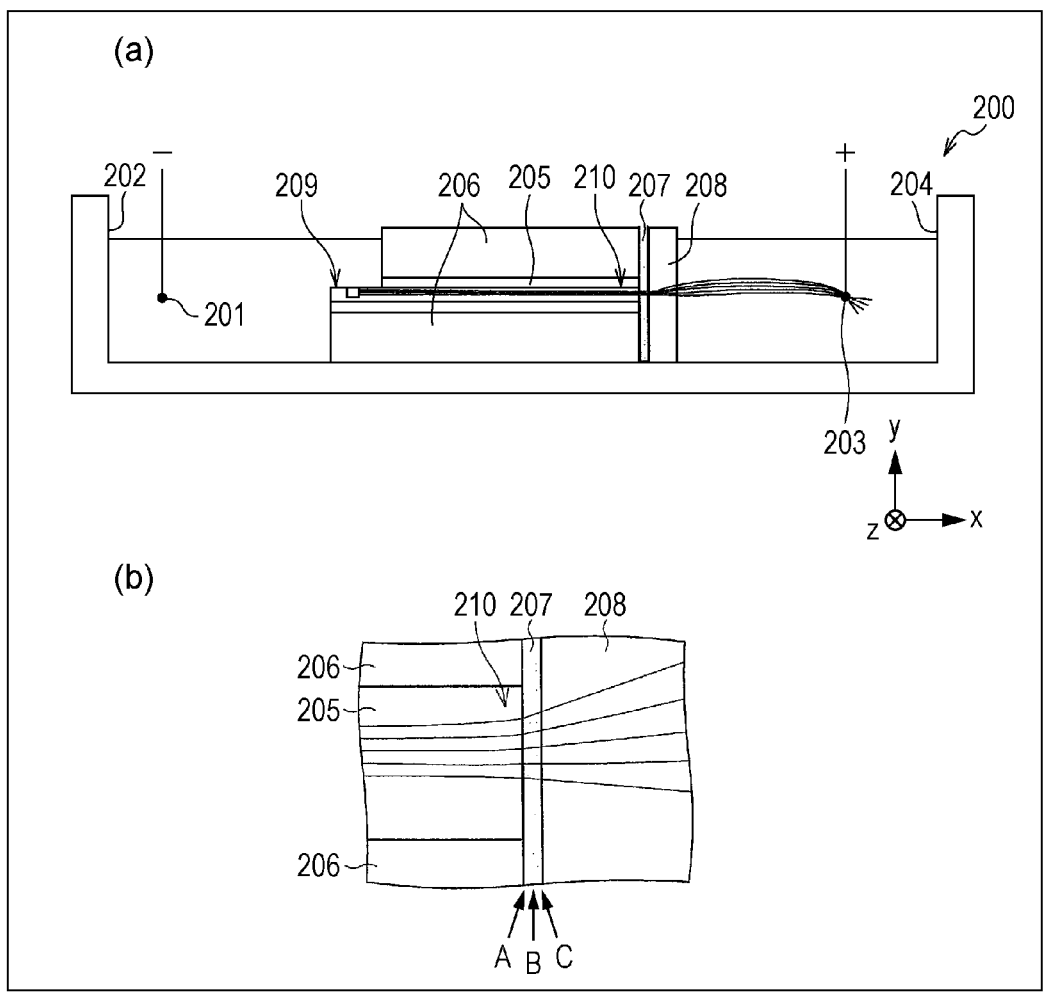
FIG. 17(a) illustrates a configuration of a model for a sample separation and adsorption appliance according to Comparative Example.
FIG. 17(b) is an enlarged view of the vicinity of a second opening in the appliance of FIG. 17(a), the view illustrating the result of a particle orbit simulation.

Settings of the sample separation and adsorption appliance 200 were the same as those in the above-described simulations except for a point of not including the slit structure. More specifically, as illustrated in FIG. 17(a), the sample separation and adsorption appliance 200 includes a first buffer solution tank 202 in which a first electrode 201 is disposed, a second buffer solution tank 204 in which a second electrode 203 is disposed, and a sample separation unit 206 containing a separation medium 205. Furthermore, a porous layer (transfer film) 207 contacting with one end of the separation medium 205, and a liquid absorption medium layer 208 supporting the porous layer 207 are disposed in the second buffer solution tank 204.

FIG. 17(a) illustrates a configuration of a model for the sample separation and adsorption appliance 200 according to Comparative Example, and FIG. 17(b) is an enlarged view of the vicinity of the second opening in the appliance illustrated in FIG. 17(a), the view illustrating the result of the particle orbit simulation.

As illustrated in FIG. 17(b), the width (dm) of the lines of electric force in the y-direction spreads to 476.2 µm at a surface of the porous layer 207 contacting with a second opening 210 (i.e., at a position A), 505.6 µm at a midpoint of the porous layer 207 (i.e., at a position B), and 535.1 µm at a surface of the porous layer 207 adjacent to the liquid absorption medium layer 208 (i.e., at a position C). Thus, it is understood that, in the sample separation and adsorption appliance 200 including no slit, the lines of electric force diffuse in width in the y-direction, and that the sample discharged from the second opening 210 is transferred to the porous layer 207 while spreading following the lines of electric force.

It is hence apparent that the sample adsorption with higher resolution can be realized with the sample separation and adsorption appliances 100 to 160 according to the embodiments.

(Fabrication of Sample Separation and Adsorption Appliance 120)

Next, the sample separation and adsorption appliance 120 illustrated in FIG. 3 was fabricated as described below, and was operated to perform continuously the electrophoresis and the transfer.

First, the sample separation unit 6 was formed using glass in dimensions of 70 mm wide×30 mm long×5 mm thick, and 13% polyacrylamide (60 mm wide×30 mm long×1.2 mm thick) containing a Bis-Tris/HCl buffer at pH 6.4 was filled as the separation gel 7 in the sample separation unit 6. At that time, a comb (having a projection of 4 mm×6 mm×1 mm) was inserted into the separation gel 7 on the side close to the first opening 17 in order to form a well (recess of 4 mm×6 mm×1 mm) for applying a sample therethrough. The second opening 18 was covered with a hydrophilic Durapore film (polyvinylidene fluoride film made by Millipore Corporation) having a thickness of 125 µm such that the separation gel 7 was fully filled up to the end of the second opening 18. The Durapore film has a much lower protein adsorption capacity (4 µg/cm$^2$) than a nylon film, a nitrocellulose film, and a PTFE (Polytetrafluoroethylene) film. It is hence regarded that even when the Durapore film is present in a path (i.e., the second opening 18) through which sample components pass during the separation and the adsorption of the sample, it does not adversely affect the separation and the adsorption of the sample.

After gelation of the polyacrylamide, the comb was removed and the sample was introduced to the well. At that time, to seal off the well and to avoid the sample from flowing out to the buffer solution in the first buffer solution tank 4, the sample was fixated by pouring 1% agarose and then gelling the agarose.

A commercially available molecular weight marker (See-Blue Plus 2 Pre-stained Standard, Invitrogen) was used as the sample.

The sample separation unit 6 was fixedly held on the stage 13 made of acrylic. To prevent heating upon application of a voltage, a cooling device (not illustrated) using a Peltier element was mounted to the underside of the stage 13 in advance. With the installation of the sample separation unit 6, the first buffer solution tank 4 was formed on the side closer to the first opening 17, and the second buffer solution tank 5 was formed on the side closer to the second opening 18. A commercially available MOPS buffer (Invitrogen) at pH 7.3 was poured into the first buffer solution tank 4 to be filled in the first buffer solution tank 4. The negative electrode 2 made of a platinum wire was then put in the first buffer solution tank 4 on the side away from the first opening 17.

Next, the transfer film 9 (i.e., a PVDF film (Immobiron PSQ) made by Millipore Corporation), having been subjected to a hydrophilizing process in advance, was inserted into the second buffer solution tank 5. One end of the transfer film 9 was held on the moving arm 10, and the other end of the transfer film 9 was wound around the transfer film storage roll 11 made of acrylic. Thereafter, a concave basin (i.e., the slit structure 8b) made of acrylic and including the slit 1, which was opened in widths of 50 µm in the x-direction, 100 µm in the y-direction, and 60 µm in the z-direction, was fitted into the second buffer solution tank 5. To avoid the bottom surface of the slit structure 8b from resting directly on the transfer film 9, the bottom surface of the second buffer solution tank 5 is raised in its opposite lateral portions (having a width of 5 mm from each lateral wall) by 3 mm from its central portion (having a width of 60 mm). Thus, the slit structure 8b was placed on the raised rail-shaped opposite lateral portions of the bottom surface, and the transfer film 9 was positioned in a space surrounded by the opposite lateral portions and the central portion of the bottom surface of the second buffer solution tank 5 and by the bottom surface of the slit structure 8b.

Thereafter, the plunger 19 was inserted between the slit structure 8b and the wall surface of the second buffer solution tank 5 opposing to the second opening 18 such that the slit 1 and the transfer film 9 were pressed against the second opening 18 and fixed in place. Then, a buffer solution prepared by mixing a commercially available NuPAGE transfer buffer (Invitrogen) at pH 7.2 with 20% methanol was poured and filled into the second buffer solution tank 5, and the positive electrode 3 made of a platinum wire was put in the second buffer solution tank 5.

After the end of the above-described preparations, electrophoresis separation was carried out by applying a voltage between the negative electrode 2 and the positive electrode 3 (at a constant current of 25 mA for 25 minutes). Because the sample "SeeBlue Plus 2 Pre-stained Standard, (Invitrogen)" was a stained protein mixture, the state of the sample under the electrophoresis could be observed visually. The moving arm 10 was operated with programming set in advance such that the lifting-up of the moving arm 10 was started upon a rise of the voltage occurred when the leading end of the migrating sample reached the second opening 18. Thus, at the same time as discharge of the sample components, the lifting-up of the moving arm 10 was automatically started at desired one of multiple changeable speeds. The voltage between the two electrodes was detected by a voltage measurement unit connected to the two electrodes.

The sample components discharged from the second opening 18 were continuously adsorbed (transferred) onto the transfer film 9, and the transfer film 9 was recovered by the moving arm 16 after the end of the transfer. As a result of visually observing the recovered transfer film 9, it was confirmed that the sample was separated and transferred satisfactorily.

The present invention is not limited to the above-described embodiments, and the present invention can be variously changed within the scope defined in Claims. Embodiments obtained by combining the technical means, disclosed in the different embodiments, with each other as appropriate are also involved within the technical scope of the present invention.

INDUSTRIAL APPLICABILITY

The present invention can be suitably used in analyses of biological samples, chemical samples, etc., and in manufacturing appliances for the analyses.

REFERENCE SIGNS LIST 1 slit
2 negative electrode
3 positive electrode
4 first buffer solution tank
5 second buffer solution tank
6 sample separation unit
7 separation gel
8 slit structure
9 transfer film
10 moving arm
12 guide
13 stage
17 first opening
18 second opening
20 projection
21 projection
100 to 160 sample separation and adsorption appliances

The invention claimed is:

1. A sample separation and adsorption appliance configured to separate a sample in a separation medium by applying a current to the separation medium through a buffer solution, and to adsorb the separated sample into a sample adsorption medium from the separation medium, the sample separation and adsorption appliance comprising:

a first electrode;
a second electrode;
a sample separator including a first opening opened to a side facing the first electrode and a second opening opened to a side facing the second electrode, and that contains the separation medium; and
a slit structure including a slit at a position facing the second opening, wherein
the sample adsorption medium is positioned between the second opening and the slit,
the slit is not provided between the second opening and the sample adsorption medium,
the sample adsorption medium is in contact with the slit,
a distance between the second opening and the slit is 300 µm or more and 4000 µm or less,
when adsorbing the separated sample into the sample adsorption medium from the separation medium, the sample adsorption medium moves in a second direction perpendicular to a first direction that extends between the first electrode and the second electrode, and
a width of the slit in the second direction is narrower than a width of the second opening in the second direction.

2. The sample separation and adsorption appliance according to claim 1, wherein an electrically conductive medium allowing the sample to pass therethrough is interposed between the second opening and the sample adsorption medium.

3. The sample separation and adsorption appliance according to claim 1, wherein
the slit structure includes a projected portion having a shape projecting toward the second opening from a periphery of the slit and entering the sample separator through the second opening; and
the slit structure is configured to hold the sample adsorption medium between the projected portion and the slit.

4. The sample separation and adsorption appliance according to claim 1, further comprising:
a first buffer solution tank in which the first electrode is arranged; and
a second buffer solution tank in which the second electrode is arranged,
wherein the slit structure is constituted integrally with the second buffer solution tank, and
at least a portion of the second buffer solution tank, the portion including the slit structure, is constituted symmetrically with respect to a plane that passes a center of the slit in a second direction perpendicular to a first direction specified by the first electrode and the second electrode, and that is perpendicular to the second direction.

5. The sample separation and adsorption appliance according to claim 1, wherein the slit structure is constituted integrally with the sample separator at a side of the sample separator closer to the second opening.

6. The sample separation and adsorption appliance according to claim 1, wherein the first electrode, the first opening, the second opening, and the second electrode are arranged substantially on one linear line.

7. The sample separation and adsorption appliance according to claim 1, further comprising a guide configured to specify a path along which the sample adsorption medium is to be moved.

8. The sample separation and adsorption appliance according to claim 1, further comprising an actuator configured to move the sample adsorption medium at the position facing the second opening in a second direction perpendicular to a first direction that is specified by the first electrode and the second electrode.

9. The sample separation and adsorption appliance according to claim 8, further comprising a voltage detector configured to detect a voltage between the first electrode and the second electrode,
   wherein the actuator starts the movement of the sample adsorption medium in accordance with the voltage detected by the voltage detector.

10. A sample separation and adsorption appliance configured to separate a sample in a separation medium by applying a current to the separation medium through a buffer solution, and to adsorb the separated sample onto a sample adsorption medium from the separation medium, the sample separation and adsorption appliance comprising:
   a first electrode;
   a second electrode;
   a sample separator including a first opening opened to a side facing the first electrode and a second opening opened to a side facing the second electrode, and that contains the separation medium; and
   a slit structure including a slit at a position facing the second opening, wherein
   the sample adsorption medium is positioned between the second opening and the slit,
   the slit structure includes a projected portion including two projections projecting toward the second opening with the slit being positioned between the two projections, and
   at least a portion of the projected portion is held in a state entering the sample separator through the second opening together with the sample adsorption medium and contacting with the separation medium while the sample adsorption medium is interposed therebetween.

* * * * *